United States Patent [19]

Goodman

[11] Patent Number: 4,878,380

[45] Date of Patent: Nov. 7, 1989

[54] METHOD OF TESTING CATALYTIC CONVERTERS AND OXYGEN SENSORS

[76] Inventor: Lynn R. Goodman, 3240 Sleeping Lady Lane, Anchorage, Ak. 99515

[21] Appl. No.: 252,386

[22] Filed: Oct. 3, 1988

[51] Int. Cl.$^4$ .......................................... G01M 15/00
[52] U.S. Cl. ..................................... 73/118.1; 73/1 G
[58] Field of Search .................... 73/118.1, 116, 117.3, 73/117, 198 A, 1 G

[56] References Cited

U.S. PATENT DOCUMENTS

| 2,968,585 | 1/1961 | Giammaria | 123/198 A X |
| 3,779,213 | 12/1973 | Knudgen | 123/198 A X |
| 4,116,053 | 9/1978 | Blanke | 73/117.3 |
| 4,369,754 | 1/1983 | Lofmkan | 123/198 A X |

FOREIGN PATENT DOCUMENTS 3634873 4/1987 Fed. Rep. of Germany ....... 73/1 G

OTHER PUBLICATIONS

1986 Chevrolet Camaro Shop Manual. St 368-86, GM Publication, p. 6E2-C1-3.

Primary Examiner—Jerry W. Myracle
Attorney, Agent, or Firm—Michael Tavella

[57] ABSTRACT

A method for testing catalytic converters is disclosed that uses optimum engine settings to determine the operational efficiency of catalytic converters. The method consists of the steps of: pre-setting the engine until it is within manufacturers operating specifications; and then injecting a subsidiary air-fuel mixture into the intake manifold which is supplied from an external source from the internal combustion engine; then adjusting the subsidiary air-fuel mixture until the exhaust gasses produced by th e internal combustion engine are equal to about: 14.7 percent Carbon Dioxide, 0.0 parts per million Hydrocarbons, and between about 1.0 and 1.4 percent Oxygen; and then finally reading the output of carbon monoxide produced by the engine when the percentage of gasses produced in proportions listed above are achieved. This test uses standard automotive test equipment that is now used for emission's testing throughout the United States. A method of testing a vehicle's oxygen sensor is also disclosed. This method uses a subsidiary air-fuel mixture to adjust that air-fuel mixture of the engine from full rich to full lean and then reading the output voltages from the oxygen sensor at the full rich and full lean points. Finally, a method of cleaning the combustion chamber is also disclosed that cleans the engine by injecting a cleaning solvent by remote elements through the intake manifold of the engine.

5 Claims, 2 Drawing Sheets

METHOD OF TESTING CATALYTIC CONVERTERS AND OXYGEN SENSORS

This invention is related to testing of catalytic converters and oxygen sensors and cleaning the combustion chamber and particularly to testing of catalytic converters and oxygen sensors and cleaning the combustion chamber using remotely attached air-fuel mixture adjustment means.

BACKGROUND OF THE INVENTION

Catalytic Converters

Since the mid 1970's, automobiles and other vehicles have had environmental controls installed to reduce the levels of pollutants released into the air. Many states now monitor the levels of emissions from vehicles to ensure that environmental standards are being met. Although testing devices, such as the type disclosed in U.S. Pat. No. 4,175,427 to Blanke, are helpful in monitoring pollutants, one important device, the catalytic converter can not be readily tested, although an accepted test has been developed. This test uses four output gasses to determine the effectiveness of the engine and the pollution controls.

The Blanke Patent discusses the primary reason that catalytic converter tests aren't done: in order to perform the test, the vehicle's engine must be adjusted and then reset. Although the Blanke patent discussed this problem, it states that it is beyond the scope of his disclosure.

Other Tests

The oxygen sensor now installed on late model vehicles can also be tested using the same air-fuel mixture adjustment techniques. This sensor is used to adjust the air-fuel mixture of the engine by meausring the combustion oxygen in the air-fuel mixture. Depending on the engine settings, this sensor will cause the air-fuel mixture to become either rich or lean as needed by the car to maintain a uniform efficiency within the engine. A malfunctioning oxygen sensor will affect the efficiency of the engine and may eventually cause the engine to run poorly. By adjusting the remote air-fuel mixture, this device can be readily tested.

The combustion chamber of the engine can also be cleaned by this method by using water that is injected into the air-fuel mixture from a remote source. In this way, excess carbon can be stripped from the combustion chamber.

DETAILED DESCRIPTION OF THE INVENTION

Figure 1:
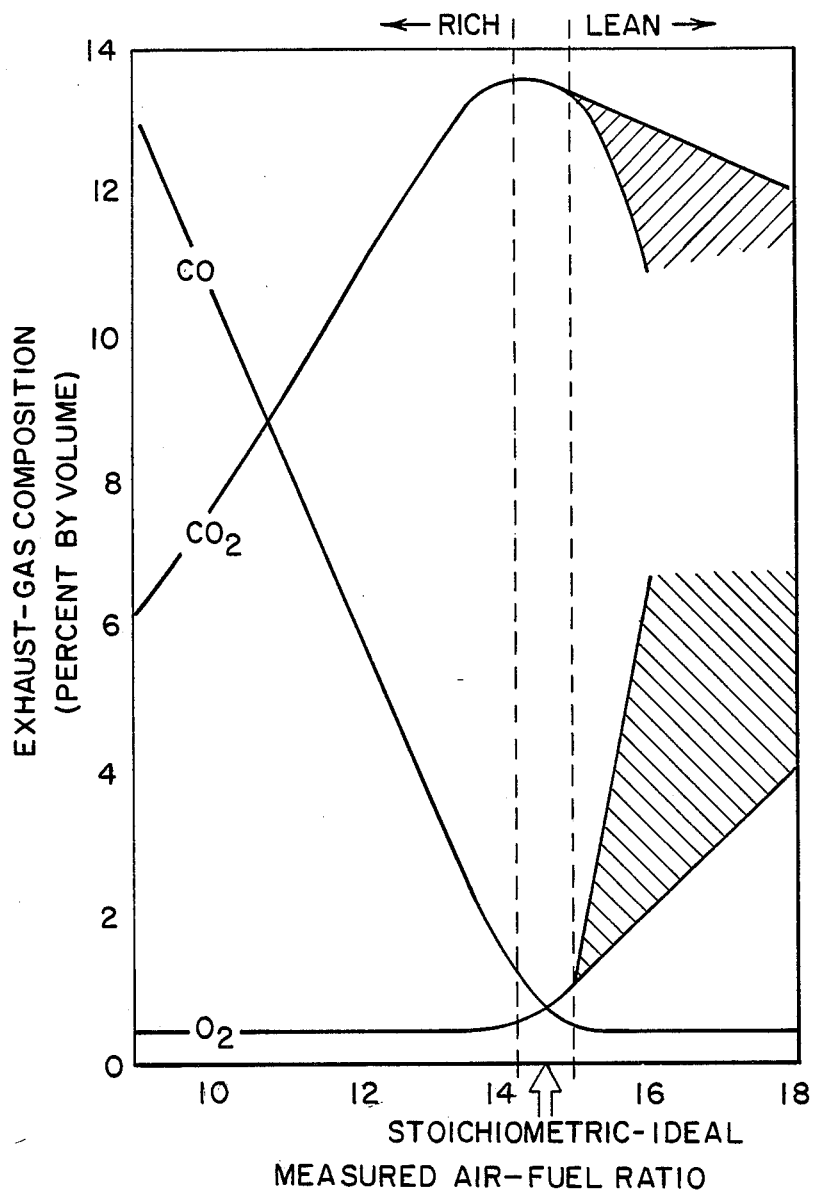
FIG. 1 is a graph of exhaust gas composition vs. measured air-fuel ratio showing the stoichiometric point.
Figure 2:
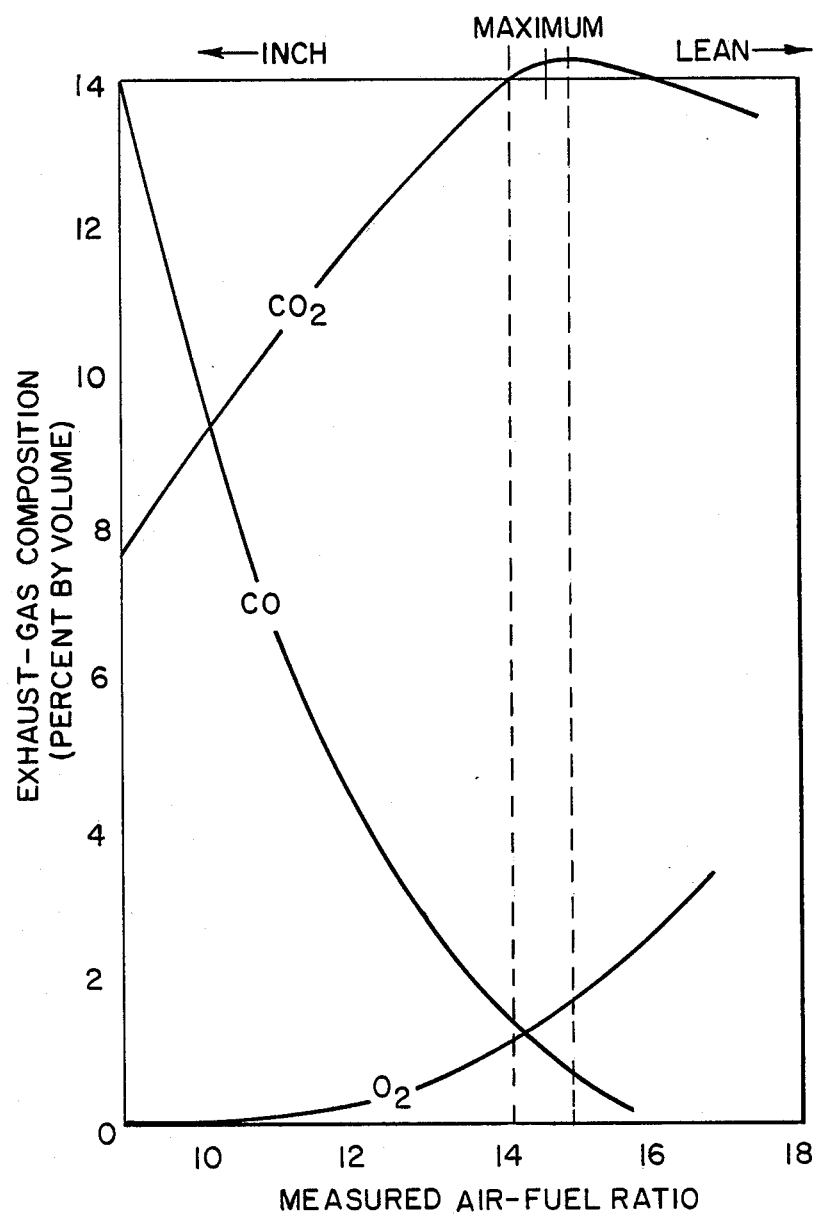
FIG. 2 is a graph of exhaust gas composition vs. measured air-fuel ratio showing the exhaust gasses when the carbon dioxide level is adjusted to the maximum achievable output level.

To understand the procedure for testing a catalytic converter, it is necessary to discuss what a typical engine does Theoretically, if gasoline is burned completely with oxygen ($O_2$) in an internal combustion engine, the products produced by the combustion are water vapor and carbon dioxide ($CO_2$). In fact, the theoretical products are never fully produced because engines do not usually run at their peak efficiency. Typically, an engine usually procues a mix of carbon monoxide (CO), $CO_2$, $O_2$, various hydrocarbon gases, and water vapor (see FIG. 1). Depending on the operating performance of any given engine, the percentage output of the four gases (CO, $CO_2$, $O_2$, and hydrocarbons) can vary considerably. Under ideal conditions, however, an engine operating at peak efficiency with a working catalytic converter will reduce $O_2$ and CO output because these gases will be adsorbed into additional $CO_2$. $CO_2$ output will be maximized and residual hydrocarbon output should be near zero (see FIG. 2). If $CO_2$ output is maximized, $O_2$ output is greater than CO output, and CO output is greater than 0.5, then the catalytic converter is defective. This condition is shown in FIG. 2. This test will show proper results only if $CO_2$ production exceeds 13.6% and $O_2$ output is slightly above 1.0% (typically 1.2–1.6%). At this level of performance, residual hydrocarbons are reduced to a minimum. A complete discussion of this theory and application can be foun in the report *MGA-90* by Sun Electric Corporation; the *California Bureau of Automative Repair Memorandum* dated June 10, 1985; and *Catalytic Convertor Test Proposal,* Municipality of Anchorage, Vehicle Inspection Program. Additionally, if an engine has been adjusted to its maximum $CO_2$ conversion capability, and the $O_2$ level is almost 0.0 percent, then the catalytic converter is totally defective. This condition relates to the internal substrate within the converter and means that there is effectively no substrate or no converter in the exhaust system.

In order to achieve the output levels needed to ensure a proper test, the air-fuel mixture feeding an engine must be adjusted to either lean or rich, as needed, until the output of the engine matches the test criteria. In all late model vehicles, this cannot be done without adjusting the carburetor or injection system. Recent car models have factory sealed adjustment screws making these adjustments difficult and problematic. Once these adjustment screws are adjusted, they must be precisely reset in order to ensure proper engine performance. Because this is a time consuming and skillful procedure, it is not practical to use this method to test catalytic converters with present day equipment.

The present invention is a method of testing that is designed to eliminate the difficulty in testing catalytic converters. The method consists of injecting either fuel or air directly into the intake manifold of an engine, adjusting the air-fuel mixture using remote monitoring and control means to reach the proper settings of $CO_2$, $O_2$, and HC, and then reading the level of CO produced.

Testing catalytic converters can be done by first ensuring that the engine is tuned properly and is operating within normal operating limits. The four output gasses are then measured to determine the base output of the engine. For example a 1984 Plymouth 2.2 liter engine produced initial values, with the air injection system operating, of:

| | |
|---|---|
| CO | .00% |
| HC | 9 ppm |
| $CO_2$ | 12.4% |
| $O_2$ | 2.0% |

The air-fuel mixture was leaned to achieve the following results:

| CO | .00% |
|---|---|
| HC | 161 ppm |
| $CO_2$ | 9.8% |
| $O_2$ | 5.1% |

The air injection system was then deleted by clamping off the air injection hose; this step produced the following readings:

| CO | 1.5% |
|---|---|
| HC | 50 ppm |
| $CO_2$ | 13.5% |
| $O_2$ | 0.3% |

The air-fuel mixture was then adjusted, while the air injection system was still disabled until the optimum outputs of $CO_2$, $O_2$ and HC were reached in order to perform the catalytic converter test. The CO reading was then established:

| CO | .06% | (less than 0.5% indicates good) |
|---|---|---|
| HC | 0 ppm | (must ensure minimum HC) |
| $CO_2$ | 14.7% | (maximum $CO_2$) |
| $O_2$ | 1.2% | ($1.0\% < O_2 < 1.5\%$) |

This test can be performed with any exhaust gas analyzer that will show the output percentages of the four gasses under test. These test devices are common to the industry.

When this test is performed, the air injection system must be blocked to ensure that supplementary oxygen is deleted from the exhaust. This can be done most effectively by shutting down the air injection system by clamping off the air injection hose. An alternative to clamping the air injection is to ensure that the exhaust system is operating properly. The control air-fuel mixture can be injected at any convenient port that accesses the intake manifold. Typically, the PCV system is often the most practical. Other ports, such as the power brake system, can also be used.

Oxygen Sensor Test

The method of adding a supplemental air-fuel mixture can also be used to test a vehicle's oxygen sensor. If a vehicle has an Assembly Line Data Link (ALDL) (an on board computer system) that will allow reading of the oxygen sensor voltage, you can use a hand held tester or compatible analyzer to directly access the ALDL to read the oxygen sensor voltage. Before performing the test, the system must be set in the closed loop configuration. On vehicles that are not equipped with an ALDL, the voltage must be read directly off the oxygen sensor. To do this, a test link must be used to access the output of the sensor. The output of the sensor is measured with a high impedance voltmeter.

Once the test leads have been installed, and the output voltages are monitored, the test can begin. By adding fuel into the engine using a remote source such as described above, the engine can be set to the richest air-fuel mixture possible. The voltage from the oxygen sensor should now be greater than 0.9 volts.

The air-fuel mixture can then be leaned out by adding oxygen into the combustion chamber to the point where the engine will almost quit running. The oxygen sensor's voltage should then read less than 0.15 volts. If the voltages read during the test are outside the limits, then the oxygen sensor is defective.

Combustion Chamber Cleaning

It is also possible to clean the combustion chamber of an engine by using the supplemental injection system. Although solvents can be used in older engines, water is the recommended cleaning agent in vehicles equipped with oxygen sensors and catalytic converters. The engine must be brought up and maintained at speeds over 2000 rpm for the duration of the cleaning. At that point, the water (or solvent) can be injected into the ports discussed above for testing catalytic converters. Once the quantity of water is injected into the engine (approximately one pint), the cleaning is complete. For excessively dirty engines, it may be necessary to repeat this process.

It is intennded that the present disclosure should not be construed in any limited sense other than that limited by the scope of the claims having regard to the teachings herein and the prior art being apparent with the preferred form of the invention disclosed herein and which reveals details of structure of a preferred form necessary for a better understanding of the invention and may be subject to change by skilled persons within the scope of the invention without departing from the concept thereof.

I claim:

1. A method for testing catalytic converters used in combination with internal combustion engines having an intake manifold, and an exhaust system, being used in vehicles, comprising the steps of:
    (a) operating the internal combustion engine to operating temperature;
    (b) injecting a subsidiary air-fuel mixture into the intake manifold, said subsidiary air-fuel mixtue being supplied from a source external to the internal combustion engine;
    (c) adjusting the subsidiary air-fuel mixture until the exhaust gasses produced by the internal combustion engine are equal to about: 14.7 percent carbon dioxide, and between about 1.0 and 1.4 percent oxygen;
    (d) reading the output of carbon monoxide produced by the engine when the percentage of gasses produced in step c are reached.

2. A method for testing catalytic converters used in combination with internal combustion engines havng an intake manifold, an air injection system and an exhaust system, being used in vehicles, comprising the steps of:
    (a) pre setting the engine until it is within manufacturers operating specifications;
    (b) deleting any oxygen added to the internal combustion engine;
    (c) injecting a subsidiary air-fuel mixture into the intake manifold, said subsidiary air-fuel mixture being supplied from a source external to the internal combustion engine;
    (d) adjusting the subsidiary air-fuel mixture until the exhaust gasses produced by the internal combustion engine are equal to about: 14.7 percent carbon dioxide, and between about 1.0 and 1.4 percent oxygen;
    (e) reading the output of carbon monoxide produced by the engine when the percentage of gasses produced in step c are reached.

3. The method of claim 2 wherein the step of deleting any oxygen from the internal combustion engine comprises the step of clamping off the air injection system.

4. The method of claim 2 wherein the step of deleting any oxygen added to the internal combustion engine comprises the step of repairing any defects in the exhaust system of the vehicle.

5. The method for testing oxygen sensing means used in combination with internal combustion engines combusting a variable internally generated air-fuel mixture, and having an intake manifold, an oxygen sensing means and an exhaust system, being use in vehicles, comprising the steps of:
   (a) connecting a test instrument calibrated to read direct current voltage to the output of the oxygen sensing means;
   (b) adjusting the air-fuel mixture to full rich by addng fuel by remote means through the intake manifold;
   (c) reading the output voltage produced by the oxygen sensing means with the test instrument;
   (d) determining whether the oxygen sensing means is operating by interpreting whether the output voltage produced by the oxygen sensing means exceeds 0.9 volts;
   (e) adjusting the air-fuel mixture to full lean by removing the remote source of fuel and substituting therefore a remote source of air;
   (f) reading the output voltage produced by the oxygen sensing means with the test instrument;
   (g) determining whether the oxygenn sensing means is operating by interpreting whether the output voltage produced by the oxygen sensing means is less than 0.15 volts.

* * * * *